United States Patent [19]

Hakansson et al.

[11] 4,431,001
[45] Feb. 14, 1984

[54] STIMULATOR SYSTEM

[75] Inventors: Bo H. Hakansson; Roy A. Saario; Roy A. Saario, both of Lund, Sweden

[73] Assignee: Crafon Medical AB, Sweden

[21] Appl. No.: 300,952

[22] Filed: Sep. 10, 1981

[30] Foreign Application Priority Data

Sep. 17, 1980 [SE] Sweden .............................. 8006523

[51] Int. Cl.$^3$ ............................................. A61N 1/36
[52] U.S. Cl. .............................. 128/421; 128/419 PS
[58] Field of Search ................. 128/24.1, 24.2, 24.5, 128/783–784, 788, 419 P, 419 PG, 419 PS, 419 PT, 419 R, 419 E, 420 R, 420 A, 421–422; 320/27–29, 47, 49, 53, 57, 59, 61–62, DIG.1–DIG. 2

[56] References Cited

U.S. PATENT DOCUMENTS

| | | | |
|---|---|---|---|
| 3,163,166 | 12/1964 | Brant et al. | 128/207.21 |
| 3,255,753 | 6/1966 | Wing | 128/421 |
| 3,454,012 | 7/1969 | Raddi | 128/422 |
| 3,547,127 | 12/1970 | Anderson | 128/421 |
| 3,783,877 | 1/1974 | Bowers | 128/421 X |
| 3,867,950 | 2/1975 | Fischell | 128/419 P |
| 3,888,260 | 6/1975 | Fischell | 128/419 P X |
| 3,902,502 | 9/1975 | Liss et al. | 128/422 |
| 3,942,535 | 3/1976 | Schulman | 128/419 PS |
| 3,946,745 | 3/1976 | Hsiang-Lai et al. | 128/421 |
| 3,954,111 | 5/1976 | Sato | 128/419 R |
| 4,082,097 | 4/1978 | Mann et al. | 128/419 PS |
| 4,096,866 | 6/1978 | Fischell | 128/419 PG |
| 4,102,347 | 7/1978 | Yukl | 128/421 |
| 4,106,511 | 8/1978 | Erlandsson | 128/422 X |

FOREIGN PATENT DOCUMENTS

| | | | |
|---|---|---|---|
| 2720331 | 11/1978 | Fed. Rep. of Germany | 128/419 PS |
| 1503915 | 10/1967 | France | |
| 2307520 | 11/1976 | France | 128/419 PS |
| 950182 | 2/1964 | United Kingdom | |

OTHER PUBLICATIONS

Evalenko et al.; "Rechargeable Implantable Cardiac Pacemaker"; *Journal of the Assoc. for the Advancement of Med. Instr.;* Mar./Apr. 1967, pp. 13–16.
Contelle; "An Effective Remedy for Women with Incontinence", 9-1982.

*Primary Examiner*—Lee S. Cohen
*Assistant Examiner*—Angela D. Sykes
*Attorney, Agent, or Firm*—Lerner, David, Littenberg, Krumholz & Mentlik

[57] ABSTRACT

An electrical stimulator system is described incorporating rechargeable batteries and a charging circuit. A charging set and electrode support are alternatively connected to the stimulator system via a single common two-pole terminal. The system is designed to prevent current from flowing directly from the battery to the electrode support along the charging circuit while allowing charge current to flow in the opposite direction along the charging circuit if the charging set is connected to the system instead of the electrode support.

13 Claims, 2 Drawing Figures

STIMULATOR SYSTEM

BACKGROUND OF THE INVENTION

The present invention relates in general to a stimulator system and, more particular, to an electrical stimulator system having a rechargeable potential source, i.e., a battery, for generating electrical stimulating pulses for the stimulation of a muscle, nerve or the like in the treatment of incontinence. More specifically, the present invention provides an electrical stimulator system suitable for use with rechargeable batteries in accordance with what is customary in other areas where rechargeable batteries are used for driving different devices such as calculators or the like. In this regard, the present invention takes into consideration the special problems which are associated with electrical stimulation for the treatment of incontinence and, more particular, with vaginal and anal stimulation.

One such electrical stimulator system is disclosed in U.S. Pat. No. 4,106,511 which includes an obturator intended to be worn within the vagina or anus. The obturator is provided with electrodes energized by a pulse generator for controlling the urethra, bladder and/or rectal functions of the wearer. However, such prior art stimulator system is constructed to use disposable batteries as a potential source for supplying power to the pulse generator. When the batteries become sufficiently discharged during use, it is required that the wearer replace these batteries before continued use is possible. It is readily apparent that the necessity for periodic replacement of such batteries presents a number of disadvantages, e.g., economic and convenience, in electrical stimulator systems of this known prior art type.

In U.S. Pat. No. 3,902,502, there is disclosed a stimulator system for temporarily arresting arthritic pain which incorporates a rechargeable battery adapted to be charged by an external charging device. When the rechargeable batteries become discharged during use, the charging device is alternatively connected to the system's common output terminals for charging the batteries through a charging circuit provided therein. A diode is provided to prevent current from the charging device from flowing through other than the charging circuit during charging of the system's batteries. However, this charging circuit arrangement is not adapted for use where the current is required to be transmissible in both directions, i.e., bipolar pulses as the diode element is adapted for use with monopolar pulses in permitting current to flow in only one direction. Further, this prior art system is not suitable for use where the system's output voltage is higher than the battery voltage. In this regard, a higher output voltage would be short circuited directly to the battery through the charging circuit.

SUMMARY OF THE INVENTION

It is broadly an object of the present invention to provide a stimulator system which overcomes or avoids one or more of the foregoing disadvantages from the use of the conventional stimulator systems heretofore mentioned. Specifically, it is within the contemplation of the present invention to provide an electrical stimulator system having a rechargeable potential source wherein the stimulator system is adapted to be coupled to an electrode support provided for receiving a plurality of electrical stimulating pulses generated by the stimulator system and alternatively to a charging device provided for charging the potential source. The stimulator system comprises means for generating a plurality of electrical stimulating pulses to be received by the electrode support when coupled to the stimulator system and a charging circuit arranged for connecting the charging device to the rechargeable potential source for charging thereof when the charging device is alternatively coupled to the stimulator system. The charging circuit includes means for preventing communication between the pulse generating means and the rechargeable potential source along the charging circuit and to prevent communication between the rechargeable potential source and the electrode support along the charging circuit when the electrode support is coupled to the stimulator system.

In accordance with the above embodiment, the charging circuit includes a voltage dependent element, an energy storage element and a resistor element arranged in operative association between the pulse generating means and the rechargeable potential source; and, a rectifier element arranged between the voltage dependent element and the rechargeable potential source.

Further in accordance with the above embodiment, the voltage dependent element is adapted to remain in a non-conducting state during generation of the stimulating pulses by the pulse generating means and wherein the electrical support and charging device are alternatively coupled to the stimulator system via a common terminal.

Still further in accordance with the above embodiment the common terminal is connected to the pulse generating means and coupled to the rechargeable potential source through the charging circuit and wherein the rechargeable potential source comprises a rechargeable battery.

Further in accordance with the present invention there is provided an electrical stimulator system comprising a pulse generator driven by a rechargeable battery. The stimulator system is adapted to generate stimulating pulses transmissible to an electrode support. The electrode support is adapted to be connected to the stimulator system via a terminal. The terminal is adapted to alternatively connect a charging set to the stimulator system for charging of the battery. Means are provided for preventing the transmission of the stimulating pulses from the pulse generator at the terminal to the battery by a circuit arranged therebetween, which circuit permits the transmission of energy from the charging set to the rechargeable battery.

In accordance with the last mentioned embodiment, the pulse transmission preventing means includes a resistor and a voltage dependent element operatively arranged in the circuit with a capacitor such that the voltage dependent element remains non-conductive during the generation of stimulating pulses by the pulse generator.

BRIEF DESCRIPTION OF THE DRAWINGS

The above description, as well as further objects, features and advantages of the present invention, will be more fully understood by reference to the following detailed description of a presently preferred, but nonetheless illustrative, stimulator system in accordance with the present invention when taken in conjunction with the accompanying drawings, wherein.

DETAILED DESCRIPTION

Figure 1:
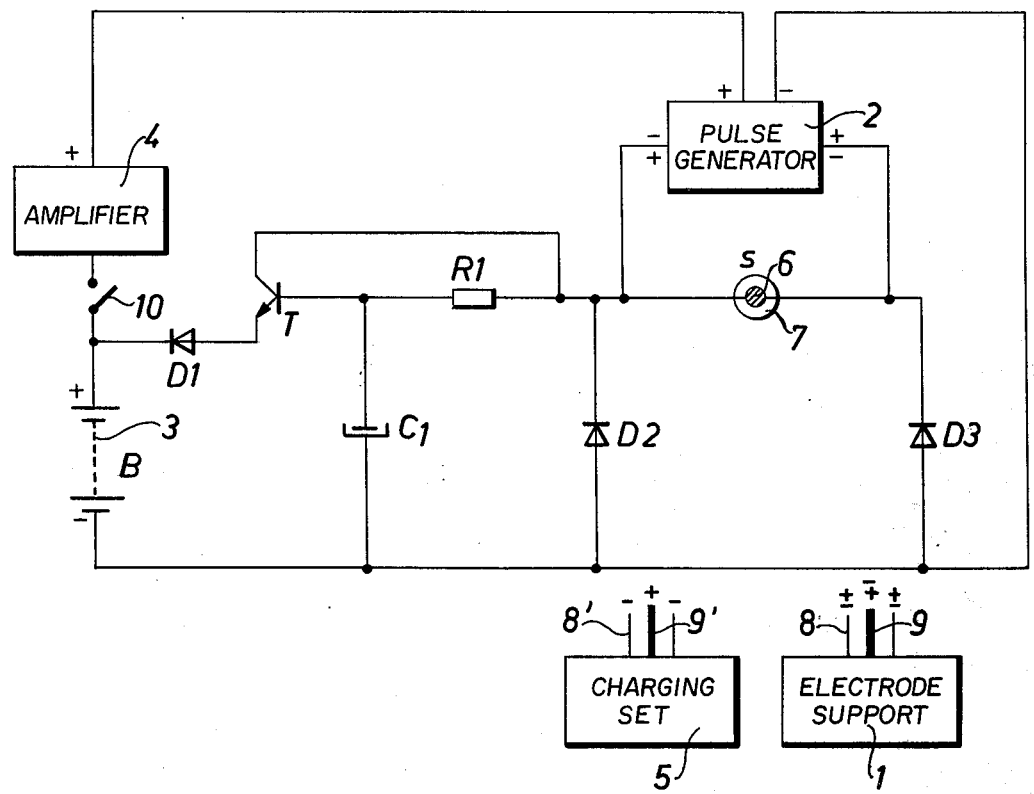
FIG. 1 shows a preferred embodiment of the stimulator system in accordance with the present invention in the form of a block diagram; and, FIG. 2 shows a pulse train suitable for the stimulator system in accordance with the present invention.

Referring specifically to the block diagram of FIG. 1, element number 1 refers to an electrode support which may be of the type described in U.S. Pat. No. 4,106,511 and U.S. Patent Application Ser. No. 97,380, filed on Nov. 26, 1979, which are respectively incorporated herein by reference. Accordingly, the electrode support 1 is not described in detail herein. When the stimulator system is used for electric stimulation, the electrode support 1 is supplied with pulses from a pulse generator 2 which in turn is driven by a rechargeable battery 3 via an amplifier 4, i.e., voltage multiplier. The electrode support 1 can be connected alternatively with a charging set 5 to a two-pole terminal S having contacts 6 and 7. In the block diagram of FIG. 1, this is indicated by means of the contacts 8 and 9 on the electrode support 1. In practice, the electrode support 1 and the charging set 5 are respectively connected appropriately with the help of a so-called teleplug which may be of identical construction for the two components. The contacts of the charging set 5 have therefore been given the designations 8' and 9'.

During charging of the rechargeable battery 3, current from the charging set 5 is isolated from the amplifier 4 and the pulse generator 2 with the help of the contact breaker 10. This isolation can be achieved manually or automatically when the charging set 5 is connected to the stimulator system. The charging set 5 is thus connected to the terminal contacts 6 and 7 via its contacts 8' and 9'. The charging current from the charging set 5 can then flow through resistor R1 and after recharging of capacitor C1 to the positive pole of battery 3 via transistor T and diode D1. The negative pole of battery 3 is connected in series with diode D3 to the corresponding pole of the charging set 5 via the terminal contact 7 and the contact $\theta'$. As such, no current will be conducted through diode D2 since the terminal contact 6 is maintained at a higher potential than the negative pole of the battery 3.

Figure 2:
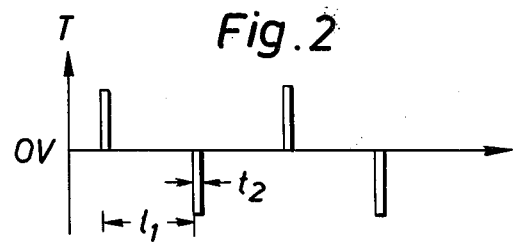

During the stimulation, the electrode support 1 is connected to terminal contacts 6 and 7 instead of the charging set 5. At the same time, the contact breaker 10 is closed so that the battery voltage is transmitted via the amplifier 4 and the pulse generator 2 to the electrode support 1. In this regard, the positive pulses would then be able to leak back to the battery 3 via resistor R1, transistor T and diode D1. However, this is prevented by choosing the magnitudes of capacitor C1 and resistor R1 in such a manner that a pulse $t_2$ (see FIG. 2) is not sufficient to charge capacitor C1 up to the voltage which is required to make transistor T conductive. During the time $t_1$, that is to say the time between pulses, capacitor C1 can be discharged. The diode D1 is provided because transistor T normally will not withstand such a high back voltage as that which it receives when the negative stimulating pulses arrive thereat. The diode D2 is provided so that symmetry is obtained for different directions of current, otherwise, symmetrical pulses are not obtained.

The stimulator system as thus described in accordance with the present invention, is constructed such that the aforementioned two-pole terminal is adapted so that it can receive alternatively the charging set 5 or the like for the charging of the battery 3. In this regard, a circuit arrangement has been provided to prevent the transmission of stimulating pulses from the common two-pole terminal to the batttery 3 via electrical components arranged in the charging circuit when the stimulator is coupled to the two-pole terminal, which circuit further permits the transmission of energy through the charging circuit from the charging set 5 to the battery when the charging set is coupled to the two-pole terminal. In the preferred embodiment, the circuit is constructed of a resistor R1 arranged in the transmission circuit together with a voltage-dependent element, e.g., transistor T, and a capacitor C1 co-ordinated with the transistor in such a manner that the transistor remains non-conducting during pulse generation by the pulse generator 2. Between the battery 3 and transistor T, a diode D1, e.g, a rectifier, is appropriately connected to prevent any direct effect upon transistor T or the electrode support 1 from the battery 3.

Preferably the stimulator system in accordance with the present invention, apart from the electrode support 1 and the charging set 5, is enclosed in a tight housing with a single outlet, which is common for receiving the electrode support and the charging set. Through the invention, considerable advantages are achieved, in particular, in connection with vaginal stimulation where the system may easily be exposed to moisture, e.g., in connection with urine leakage on confinement to a bed. Moreover, the stimulation system can be provided with a completely tight housing with only one opening, i.e., terminal S, as a result of which there should be no problem in achieving a satisfactory seal. If for this purpose a so-called teleplug with two poles is used, this may be identical as noted for the charging set 5 and the electrode support 1.

In spite of a very simple arrangement, the stimulator system is adapted so that the current is prevented from flowing directly from the battery 3 to the electrode support 1, whilst charging current may flow in the opposite direction if the charging set 5 is applied instead of the electrode support. At the same time, though, stimulator pulses are prevented from passing along the same path as the charging current. Any leakage in this direction is stopped by the aforementioned capacitor. Further, it is a considerable advantage that the system can be arranged so that the charging set 5 can never be applied at the same time as the stimulator. Thus a patient can never be subjected to the direct effect of the charging set 5.

It should be noted that in stimulating human tissues a bipolar stimulation is preferred, that is current flows for one-half cycle in one direction, and in the second half-cycle, in the opposite direction. In this manner, no electrolysis occurs and hence no effect is produced on electrodes or tissues. This entails an additional difficulty in that positive as well as negative pulses must be prevented from leaking back to the battery, which problem has been overcome by the construction of the stimulator system in accordance with the present invention.

EXAMPLE

A suitable stimulator system in accordance with the present invention is obtained when the following electric quantities are chosen for the system.

$t_1 = 50$ ms
$t_2 = 1$ ms
$R_1 = 22$ Ohm $C_1 = 3.3$ uF
$D_1 = D_2 = D_3 = 1N4148$ (Siemens)
T = BC 167 (Siemens)
B = 6 V (5×1.2 V NiCd 70 mAh) (Gould)

It is contemplated that these values can be varied within wide limits without exceeding the scope of the present invention. Similarly, of course, other sources of such components can be used. If a rechargeable unit is to be constructed, it is an object of such construction to reduce the number of rechargeable batteries, i.e., cells required. This is, on the one hand, for reasons of economy, and on the other hand, for reasons of space. It is also known that the energy content per volume diminishes with decreasing cell size.

For a vaginal stimulator of the type which is described in the above-mentioned patent and patent application, a system output voltage in the order of magnitude of 15 V is required. Without voltage amplifier 4, a large number of battery cells would be required for this purpose. This number of cells can be reduced due to the voltage amplifier 4, which is particularly important, if the stimulator is to be portable. It is possible to bring about the application of bipolar pulses with the use of two voltage units with two sets of battery cells and a doubler. In practice, it is simple to employ two transistors which alternately supply pulses via two diodes to the electrode support 1.

The actual generation of pulses can be achieved in a number of different ways. Accordingly, such pulse generation does not constitute a direct part of the present invention and is therefore not described in detail herein. The essential point is that, in accordance with the present invention, a pulse generator 2 must be provided and that the pulses generated by the generator must be prevented from getting back to the battery 3 via resistor $R_1$, transistor T and diode $D_1$.

Naturally, the invention is not simply limited to the embodiment described above but can be varied within the scope of the following claims. Thus, it will be obvious to those versed in the art that other types of delay circuits can also be used for preventing pulses intended for the electrode support from reaching the battery instead; and, the present invention can also be applied to other types of pulse generating electrode support systems.

What is claimed is:

1. An electrical stimulator system having a rechargeable potential source, said stimulator system coupled to an electrode support provided for receiving a plurality of electrical stimulating bipolar pulses generated by said stimulator system and alternatively to a charging device provided for charging said rechargeable potential source, said stimulator system comprising, generating means for generating a plurality of electrical stimulating bipolar pulses to be received by said electrode support when coupled to said stimulator system, and a charging circuit arranged between said generating means and said rechargeable potential source for connecting said charging device to said rechargeable potential source for charging thereof when said charging device is alternatively coupled to said stimulator system, said charging circuit including a voltage dependent element connected through the parallel combination of an energy storage element and a resistor element between said pulse generating means and said rechargeable potential source and means for preventing communication between said bipolar pulse generated by said generating means and said rechargeable potential source along said charging circuit when said electrode support is coupled to said stimulator system while permitting communication between said rechargeable potential source and said charging device along said charging circuit when said charging device is alternatively coupled to said stimulator system.

2. The electrical stimulator system as set forth in claim 1 wherein said charging circuit further includes a rectifier element arranged between said voltage dependent element and said rechargeable potential source.

3. The electrical stimulator system as set forth in claim 1 or 2 wherein said voltage dependent element remains in a non-conducting state during generation of said stimulating pulses by said pulse generating means.

4. The electrical stimulator system as set forth in claim 1 or 2 wherein said electrode support and said charging device are alternatively coupled to said stimulator system through a common terminal.

5. The electrical stimulator system as set forth in claim 4 wherein said common terminal is connected to said pulse generating means and connected to said rechargeable potential source via said charging circuit.

6. The electrical stimulator system as set forth in claim 1 or 2 wherein said rechargeable potential source comprises a rechargeable battery.

7. An electrical stimulator system comprising a charging circuit, a bipolar pulse generator driven by a rechargeable battery, and stimulator system generating stimulating bipolar pulses transmissible to an electrode support, said electrode support connected to said stimulator system via a terminal, said terminal alternatively connecting a charging set to said stimulator system for charging of said battery along said charging circuit, and pulse transmission prevention means for preventing the transmission of said stimulating bipolar pulses from said bipolar pulse generator to said battery by said charging circuit arranged therebetween while permitting the transmission of energy from said charging set to said rechargeable battery along said charging circuit when said charging set is alternatively connected to said terminal, said pulse transmission preventing means including a resistor and a voltage dependent element operatively arranged in said charging circuit with a capacitor such that said voltage dependent element remains non-conductive during the generation of stimulating pulses by said pulse generator.

8. The electrical stimulator system as set forth in claim 7 wherein said stimulator system, apart from said electrode support and said charging set, is enclosed in a tight housing with a single outlet terminal which preventing alternative common communication with said electrode support and said charging set.

9. The electrical stimulator system as set forth in claim 7 further including a rectifier connected between said battery and said voltage dependent element preventing interference communication therebetween and preventing interference communication between said battery and said electrode support.

10. An electrical stimulator system including a rechargeable potential source having an output at a first potential, said stimulator system be coupled to an electrode support which receives a plurality of electrical stimulating pulses generated by said stimulator system and alternatively to a charging device which charges said rechargeable potential source, said stimulator system comprising generating means for generating a plurality of electrical stimulating pulses at a second potential greater than said first potential received by said electrode support when coupled to said stimulator system, a voltage multiplier arranged between said rechargeable potential source and said generating means said voltage multiplier increasing said first potential of said rechargeable potential source to said second potential of said stimulating pulses, and a charging circuit arranged between said generating means and said rechargeable potential source connecting said charging device to said rechargeable potential source for charging thereof when said charging device is alternatively coupled to said stimulator system, said charging circuit including means for preventing communicating between said pulses generated by said generating means at said second potential and said rechargeable potential source at said first potential along said charging circuit when said electrode support is coupled to said stimulator system while permitting communication between said rechargeable potential source and said charging device along said charging circuit when said charging device is alternatively coupled to said stimulator system.

11. The electrical stimulator system of claim 10 wherein said electrical stimulating pulses are bipolar pulses.

12. The electrical stimulator system of claim 10 wherein said electrode support and said charging device are alternatively coupled to said stimulator system through a common terminal.

13. The electrode stimulator system of claim 10 wherein the preventing means of said charging circuit includes a voltage dependent element connected through the combination of an energy storage element charged through its connection with a resistor element and arranged between said generating means and said rechargeable potential source.

* * * * *

UNITED STATES PATENT AND TRADEMARK OFFICE
CERTIFICATE OF CORRECTION

PATENT NO. : 4,431,001
DATED : February 14, 1984
INVENTOR(S) : Bo H. Hakansson, Roy A. Saario It is certified that error appears in the above-identified patent and that said Letters Patent are hereby corrected as shown below:

On the title page, in the listing of inventors, delete "Roy A. Saario" second occurrence.

Column 3, line 42, "0'" should read -- 9' --.

Column 6, lines 50-51, "preventing" should read -- provides --.

Column 6, line 61, cancel the word "be".

Signed and Sealed this

Twenty-ninth Day of May 1984

[SEAL]

Attest:

GERALD J. MOSSINGHOFF

Attesting Officer

Commissioner of Patents and Trademarks